United States Patent
Saelinger et al.

(10) Patent No.: US 9,801,379 B2
(45) Date of Patent: Oct. 31, 2017

(54) METHOD FOR CONTROLLING PESTS IN SOYBEAN

(71) Applicant: BASF SE, Ludwigshafen (DE)

(72) Inventors: Daniel Saelinger, Ludwigshafen (DE); Joachim Dickhaut, Heidelberg (DE); Karsten Koerber, Eppelheim (DE); Wolfgang von Deyn, Neustadt (DE); Raffael Koller, Zurich (CH); Arun Narine, Mannheim (DE); Jean-Yves Wach, Mannheim (DE); Jochen Dietz, Karlsruhe (DE)

(73) Assignee: BASF SE, Ludwigshafen (DE)

(*) Notice: Subject to any disclaimer, the term of this patent is extended or adjusted under 35 U.S.C. 154(b) by 0 days.

(21) Appl. No.: 15/121,498

(22) PCT Filed: Feb. 25, 2015

(86) PCT No.: PCT/EP2015/053872
§ 371 (c)(1),
(2) Date: Aug. 25, 2016

(87) PCT Pub. No.: WO2015/128338
PCT Pub. Date: Sep. 3, 2015

(65) Prior Publication Data
US 2016/0366889 A1    Dec. 22, 2016

Related U.S. Application Data

(60) Provisional application No. 61/945,149, filed on Feb. 27, 2014.

(30) Foreign Application Priority Data

Mar. 7, 2014 (EP) .................................. 14158379

(51) Int. Cl.
*A01N 43/08* (2006.01)
*A01N 43/90* (2006.01)
*A01N 43/16* (2006.01)
*A01N 65/00* (2009.01)

(52) U.S. Cl.
CPC ............ *A01N 43/90* (2013.01); *A01N 43/16* (2013.01); *A01N 65/00* (2013.01)

(58) Field of Classification Search
CPC ...................................................... A01N 43/90
USPC ........................................................ 514/468
See application file for complete search history.

(56) References Cited

U.S. PATENT DOCUMENTS

2016/0262386 A1*   9/2016   Sikuljak ................. A01N 37/46

FOREIGN PATENT DOCUMENTS

| CN | 1398524 A | * 4/2002 | ............ A01N 65/00 |
|---|---|---|---|
| CN | 1398524 | 2/2003 | |
| CN | 102379296 | 3/2012 | |
| WO | WO 2012140207 | 10/2012 | |

OTHER PUBLICATIONS

[On-line] http://corn.agronomy.wisc.edu/Management/pdfs/A3890.pdf, (2009), retrieved Dec. 9, 2016, XP55263619.
International Search Report, issued in PCT/EP2015/053872, dated Apr. 13, 2015.
International Preliminary Report on Patentability, issued in PCT/EP2015/053872, dated Jun. 13, 2016.
Search Report, issued in EP 14158379.9, dated May 15, 2014.

* cited by examiner

Primary Examiner — Nizal Chandrakumar
(74) Attorney, Agent, or Firm — Brinks Gilson & Lione

(57) ABSTRACT

A method for controlling pests of soybean plants comprises the step of contacting the soybean plant, parts of it, its propagation material, the pests, their food supply, habitat or breeding grounds with one or more components of the ginkgo tree selected from the group consisting of bilobalide, ginkgolide A, ginkgolide B, ginkgolide C, ginkgolide J and ginkgolide M.

10 Claims, No Drawings

METHOD FOR CONTROLLING PESTS IN SOYBEAN

This application is a National Stage application of International Application No. PCT/EP2015/053872, filed Feb. 25, 2015, which claims the benefit of U.S. Provisional Application No. 61/945,149, filed Feb. 27, 2014. This application also claims priority under 35 U.S.C. §119 to European Patent Application No. 14158379.9, filed Mar. 7, 2014.

The invention relates to methods of pest control by insecticidal components of the ginkgo tree.

Faboideae, such as soybeans (Glycine max) and lima beans (Phaseolus lunatus), are important commercial crops.

Soybeans are considered to be a source of complete protein (Henkel, J., 2000, "Soy: Health Claims for Soy Protein, Question About Other Components". FDA Consumer (Food and Drug Administration 34 (3): 18-20). For this reason, soy is a good source of protein. According to the US Food and Drug Administration, soy protein products can be good substitutes for animal products because soy offers a 'complete' protein profile. Soy protein products can replace animal-based foods which also have complete proteins but tend to contain more fat, especially saturated fat without requiring major adjustments elsewhere in the diet.

Soybean protein isolate is highly valuable as it has a biological value of 74 (Protein Quality Evaluation: Report of the Joint FAO/WHO Expert Consultation. Bethesda, Md. (USA): Food and Agriculture Organization of the United Nations (Food and Nutrition Paper No. 51). December 1989).

In agriculture soybeans can produce at least twice as much protein per acre than some other major vegetable or grain crop, e.g. 5 to 10 times more protein per acre than land set aside for grazing animals to make milk, and up to 15 times more protein per acre than land set aside for meat production ("Soy Benefits", National Soybean Research Laboratory, February 2012).

Thus, soybeans can be regarded as a globally important crop providing oil and protein.

Nevertheless, soybean plants are vulnerable to a wide range of bacterial diseases, fungal diseases, viral diseases and parasites. Soybeans are considered to be e.g. the secondmost valuable agricultural export in the United States behind corn.

Consequently, in view of the importance of soybean in agriculture, proper pest management is required in order not to jeopardize yield and quality of the soybean crops.

Stink bugs (order of Hemiptera, family of Pentatomidae) are animal pests and true bugs. They are probably one of the most common pest problems in soybean (Stewart et al., Soybean Insects—Stink bugs, University of Tennessee Institute of Agriculture, W200 09-0098).

Stink bugs feed on over 52 plants, including native and ornamental trees, shrubs, vines, weeds, and many cultivated crops such as corn and cotton, as well as numerous uncultivated plants, and their preferred hosts are nearly all wild plants. They build up on these hosts and move to soybeans late in the season as their preferred foods mature.

Stink bugs may feed on many parts of the plant; however, they typically target developing seed including the pods, meaning that injury to soybean seed is the primary problem associated with stink bug infestations.

Brown or blackish spots may occur where their mouthparts penetrate the plant tissue, but little external signs of feeding injury may be present. Feeding may cause deformation, shriveling or abortion of small seed. Larger seed may only be partly discolored by feeding injury, but this can affect seed quality. High levels of seed abortion may cause the "green bean effect" where foliage is retained and plant maturity is delayed (Stewart et al., Soybean Insects—Stink bugs, University of Tennessee Institute of Agriculture, W200 09-0098).

Stink bugs inflict mechanical injury to the seed as well as transmitting the yeast-spot disease organism. The degree of damage caused by this pest depends to some extent on the developmental stage of the seed when it is pierced by the stink bug's needlelike mouthparts. The younger the seed when damaged, the greater the yield reduction. Although late season infestations may not affect yield, bean oil content and germination will be reduced.

In certain regions the green stink bug (*Acrosternum hilare*) is one of the most common species that feeds on soybean. The brown stink bug (*Euschistus servus*) is another common component of the stink bug complex.

Of the complex of sucking bugs that occur in cultivation, the brown stinkbug *Euschistus heros* is currently considered to be the most abundant species in northern Parana to Central Brazil (Correa-Ferreira & Panizzi, 1999), and is a significant problem in soybean (Schmidt et al., 2003). The bugs occur in soybeans from the vegetative stage and are harmful from the beginning of pod formation until grain maturity. They cause damage to the seed (Galileo & Heinrichs 1978, Panizzi & Slansky Jr., 15, 1985) and can also open the way to fungal diseases and cause physiological disorders, such as soybean leaf retention (Galileo & Heinrichs 1978, Todd & Herzog, 1980).

Other plant feeding species that may be present include the red-shouldered stink bug (*Thyanta custator*) and the dusky-brown stink bug (*Euschistus tristigmus*). Another species, the southern green stink bug (*Nezara viridula*), is often confined to the southernmost counties of the US. Predatory (beneficial) stink bugs such as the spined soldier bug (*Podisus Maculaventris*) may also be found in soybean and are sometimes mistaken for brown or dusky-brown stink bugs.

Control of stinkbugs in soybean is often vital to prevent significant economic damage.

Insecticides commonly used to control stinkbugs include pyrethroids, neonicotinoids and organophosphates, though pyrethroid insecticides are usually the method of choice for controlling stink bugs in soybean. However, there are increasing problems with insecticide resistance, particularly in brown stink bug populations and particularly to pyrethroids. *Euschistus heros* can also be difficult to manage using organophosphates or endosulfan (Sosa-Gomez et al., 2009). There is therefore a need for effective ecological methods of controlling stinkbugs in soybean.

Particularly insecticides acting on the gamma-aminobutyric acid (GABA)-gated chloride channel (disclosed in e.g. WO 2005/085216 (EP 1 731 512), WO 2009/002809 and WO 2009/080250) seem to be effective for controlling stinkbugs, especially in soybean such as described in WO2012/104331.

It has now been found that specific natural components of the ginkgo tree provide an efficient control against pests on Faboideae, in particular soybeans, especially against pests from the families of Pentatomidae and Thripidae.

These compounds therefore represent an important solution for controlling pests of Faboideae, in particular soybeans, in particular pests from the family of pentatomidae, stink bugs, and thereby safeguarding plants, crops and propagation material from the infestation by such pests, particularly where the pests are resistant to current methods.

An acaricidal activity of ginkgolide C is disclosed in CN 102379296 (A). WO 2005/025587 discloses an insecticidal activity of mixtures of ginkgolide A, B and bilobalide against two spotted spider mites and green peach aphid. WO 2004/034853 discloses insecticidal mixtures of bilobalide, ginkgolide A, B or C and unspecified derivatives thereof with organophosphates and pyrethroids against rice pests.

None of these documents discloses an acceptable efficacy of bilobalide or ginkgolides against typical pests of Faboideae, preferably soybeans, in particular stink bugs. As stated above, these pests are difficult to control with typical soybean pesticides.

Accordingly, in one aspect of the invention there is provided a method for controlling pests of Faboideae, in particular soybean plants, comprising the step of contacting the Faboideae, in particular soybean, plant, parts of it, its propagation material, the pests, their food supply, habitat or breeding grounds with one or more components of the ginkgo tree selected from the group consisting of bilobalide, ginkgolide A, ginkgolide B, ginkgolide C, ginkgolide J and ginkgolide M.

In a further aspect of the invention there is provided the use of one or more components of the ginkgo tree selected from the group consisting of bilobalide, ginkgolide A, ginkgolide B, ginkgolide C, ginkgolide J and ginkgolide M for controlling pests in Faboideae, in particular soybean crops.

In a further aspect of the invention there is provided a method for controlling pests from the family of Pentatomidae and/or Thripidae, comprising the step of contacting the pests, their food supply habitat and/or breeding ground with one or more components of the ginkgo tree selected from the group consisting of bilobalide, ginkgolide A, ginkgolide B, ginkgolide C, ginkgolide J and ginkgolide M.

In yet a further aspect of the invention there is provided the use of one or more components of the ginkgo tree selected from the group consisting of bilobalide, ginkgolide A, ginkgolide B, ginkgolide C, ginkgolide J and ginkgolide M for controlling pests from the family of Pentatomidae and/or Thripidae.

Bilobalide and the ginkgolides are known components of the ginkgo tree having the following structures:

a) Bilobalide:

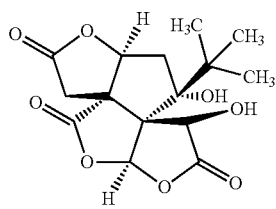

Bilobalide is the common name for (3aS,5aR,8aS,9R,10aR)-9-tert-butyl-8,9-dihydroxydihydro-9H-furo[2,3-b]furo[3',2';2,3]cyclopenta[1,2-c]furan-2,4,7(3H,8H)-trione (CAS 33570-04-6).

b) Ginkgolides:

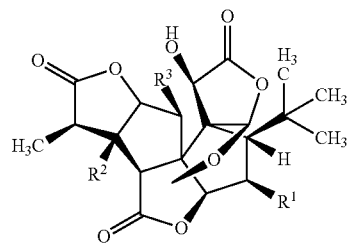

| Ginkgolide | $R^1$ | $R^2$ | $R^3$ | CAS |
|---|---|---|---|---|
| Ginkgolide A | —H | —OH | —H | 15291-75-5 |
| Ginkgolide B | —H | —OH | —OH | 15291-77-7 |
| Ginkgolide C | —OH | —OH | —OH | 15291-76-6 |
| Ginkgolide J | —OH | —OH | —H | 15291-79-9 |
| Ginkgolide M | —OH | —H | —OH | 15291-78-8 |

The above compounds can be used in pure form, as mixtures or in the form of extracts of ginkgo leaves, which may be enriched with the above compounds to a certain degree.

The compounds are commercially available, or can be obtained, preferably from ginkgo leaves by methods known in the art and described e.g. in U.S. Pat. No. 5,700,468, EP-A 360 556, EP-A 0 431 535 and JP-A 09-110713.

Further, the compounds bilobalide (in enantiopure form), ginkgolide A (in its racemic form) and ginkgolide B (in its racemic form) can be obtained by chemical synthesis, as disclosed e.g. in Tetrahedron Letters (1988), 29(28), 3423-6, Tetrahedron Letters (1988), 29(26), 3205-6 and Journal of the American Chemical Society (2000), 122(35), 8453-8463, respectively.

The methods and uses of the invention are for controlling and/or preventing infestation of Faboideae plants, Faboideae crops and Faboideae propagation material by pests. In one preferred embodiment, the Faboideae plants, crops or propagation material are soybean plants, crops or propagation material. In another preferred embodiment, the Faboideae plants, crops or propagation material are lima bean plants, crops or propagation material. In general the pests are from the family of Pentatomidae and/or Thripidae. Preferably the methods and uses of the present invention are applied against pests from the family of Pentatomidae, stink bugs. More preferably against stink bugs that are resistant to other insecticides, e.g. pyrethroid insecticides. Stinkbugs that are "resistant" to a particular insecticide refers e.g. to strains of stinkbugs that are less sensitive to that insecticide compared to the expected sensitivity of the same species of stinkbug. The expected sensitivity can be measured using e.g. a strain that has not previously been exposed to the insecticide.

In one aspect of the present invention, the method comprises applying to Faboideae plants, crops and/or propagation material, in particular soybean plants, soybean crops and/or propagation material of soybean plants or lima bean plants, lima bean crop and/or propagation material of lima bean plants, a compound of the invention, wherein the method is for controlling and/or preventing infestation by pests.

Especially the method is for controlling and/or preventing infestation by pests from the family of Pentatomidae and/or Thripidae (such as Dichromothrips like Dichromothrips corbetti), in particular from the family of Pentatomidae, stink bugs; even more particular for controlling and/or preventing infestation by *Acrosternum* spp., *Euschistus* spp., *Nezara* spp. and/or *Piezodrus* spp., most particularly by *Acrosternum hilare, Euschistus heros, Nezara viridula* and/or *Piezodrus guildini*, and especially by *Euschistus heros*. Further Pentatomidae pests that can be controlled according to the invention are *Eysarcoris*, in particular *Eysarcoris aeneus* (forest shield bug). Further Heteroptera pests that can be controlled according to the invention include Miridae, such as *Trigonotylus* like *Trigonotylus caelestialium* (rice leaf bug).

A further aspect the invention provides the use of the compounds of the invention for the general control of pests from the family of Pentatomidae (stink bugs) and/or Thripidae, preferably for the control of pests from the family of Pentatomidae, in particular for the control of *Acrosternum* spp., *Euschistus* spp., *Nezara* spp. and/or *Piezodrus* spp., more preferably for the control of *Acrosternum hilare, Euschistus heros, Nezara viridula* and/or *Piezodrus guildini*, and most preferably for the control of *Euschistus heros*.

In another aspect, the present invention provides the use of the compounds of the invention for controlling pests that are resistant to one or more other insecticides, preferably pyrethroids, neonicotinoids and organophosphates, and more preferably pyrethroid insecticides.

Preferably the compounds of the invention are used for controlling pests from the family of Pentatomidae, stinkbugs, that are resistant to one or more other insecticides, preferably pyrethroids, neonicotinoids and organophosphates, and more preferably pyrethroid insecticides, in particular for the control of *Acrosternum* spp., *Euschistus* spp., *Nezara* spp. and/or *Piezodrus* spp., preferably for the control of *Acrosternum hilare, Euschistus heros, Nezara viridula* and/or *Piezodrus guildini*, and most preferably for the control of *Euschistus heros* that are resistant to one or more other insecticides, preferably pyrethroids, neonicotinoids and organophosphates, and more preferably pyrethroid insecticides.

The compounds of the invention are bilobalide, ginkgolide A, ginkgolide B, ginkgolide C, ginkgolide J and ginkgolide M or mixtures of one or more of these compounds. Preferred are bilobalide and/or ginkgolide A.

Pests

The compounds applied in the methods of the invention may be used on Faboideae, in particular soybean or lima beans, to control, for example:

*Elasmopalpus lignosellus, Diloboderus abderus, Diabrotica speciosa, Sternechus subsignatus,* Formicidae, *Agrotis ypsilon, Julus* ssp., *Anticarsia gemmatalis, Megacopta* spp., *Megascelis* ssp., *Procornitermes* ssp., Gryllotalpidae, *Nezara viridula, Piezodorus* spp., *Acrosternum* spp., *Neomegalotomus* spp., *Cerotoma trifurcata, Popillia japonica, Edessa* spp., *Liogenys fuscus, Euschistus heros, stem borer, Dectes* spp., *stalk borer, Scaptocoris castanea, phyllophaga* spp., *Pseudoplusia includens, Spodoptera* spp., *Bemisia tabaci, Agriotes* spp., Thripidae, preferably *Diloboderus abderus, Diabrotica speciosa, Nezara viridula, Piezodorus* spp., *Acrosternum* spp., *Cerotoma trifurcata, Popillia japonica, Euschistus heros, phyllophaga* spp., *Agriotes* spp., and *Dectes texanus*.

The compounds of the invention are preferably used on Faboideae, in particular soybean or lima beans, to control stinkbugs, e.g. *Nezara* spp. (e.g. *Nezara viridula, Nezara antennata, Nezara hilaris*), *Piezodorus* spp. (e.g. *Piezodorus guildinii*), *Acrosternum* spp. (e.g. *Acrosternum hilare*), *Euschistus* spp. (e.g. *Euschistus heros, Euschistus servus*), *Halyomorpha halys, Megacopta cribaria, Plautia crossota, Riptortus clavatus, Rhopalus msculatus, Antestiopsis orbitalus, Dectes texanus, Dichelops* spp. (e.g. *Dichelops furcatus, Dichelops Melacanthus*), *Eurygaster* spp. (e.g. *Eurygaster intergriceps, Eurygaster maurd*), *Oebalus* spp. (e.g. *Oebalus mexicana, Oebalus poecilus, Oebalus pugnase, Scotinophara* spp. (e.g. *Scotinophara lurida, Scotinophara coarctatd*). Preferred targets include *Acrosternum hilare, Antestiopsis orbitalus, Dichelops furcatus, Dichelops melacanthus, Euschistus heros, Euschistus servus, Megacopta cribaria, Nezara viridula, Nezara hilare, Piezodorus guildinii, Halyomorpha halys*. In one embodiment the stinkbug target is *Nezara viridula, Piezodorus* spp., *Acrosternum* spp., *Euschistus heros. Euschistus* and in particular *Euschistus heros* are the preferred targets.

Further Pentatomidae pests that can be controlled according to the invention are *Eysarcoris*, in particular *Eysarcoris aeneus*.

Applications

Application of the compounds of the invention is preferably to a crop of Faboideae, such as soybean or lima bean plants, the locus thereof or propagation material thereof. Preferably application is to a crop of Faboideae, such as soybean or lima bean plants or the locus thereof, more preferably to a crop of soybean plants. Application may be before infestation or when the pest is present. Application of the compounds of the invention can be performed according to any of the usual modes of application, e.g. foliar, drench, soil, in furrow etc. Control of stinkbugs can be achieved by foliar application, which is a preferred mode of application according to the invention.

In another preferred embodiment, the compounds of the invention are applied to Faboideae crops by soil-drench application. In one preferred embodiment, the Faboideae crops are soybean crops. In another preferred embodiment the Faboideae crops are lima bean crops.

In a further preferred embodiment the compounds of the invention are applied as seed-treatment to seeds of Faboideae crops. In one preferred embodiment, the Faboideae crops are soybean crops. In another preferred embodiment the Faboideae crops are lima bean crops.

The pest, e.g. the stink bugs, the plant, soil or water in which the plant is growing can be contacted with the compounds of the invention or composition(s) containing them by any further application method known in the art. As such, "contacting" includes both direct contact (applying the compounds/compositions directly on the animal pest or plant—typically to the foliage, stem or roots of the plant) and indirect contact (applying the compounds/compositions to the locus of the animal pest or plant).

The compounds of the invention or the pesticidal compositions comprising them may be used to protect growing plants and crops from attack or infestation by animal pests, especially from stink bugs, in particular from *Euschistus*, more particularly from *E. heros*, by contacting the plant/crop with a pesticidally effective amount of compounds of the invention. The term "crop" refers both to growing and harvested crops.

The compounds of the invention may be applied in combination with an attractant. An attractant is a chemical that causes the insect to migrate towards the location of application. For control of stinkbugs it can be advantageous to apply the compounds of the invention with an attractant, particularly when the application is foliar. Stinkbugs are often located near to the ground, and application of an attractant may encourage migration up the plant towards the active ingredient.

Suitable attractants include glucose, sacchrose, salt, glutamate, citric acid, soybean oil, peanut oil and soybean milk. Glutamate and citric acid are of particular interest, with citric acid being preferred.

An attractant may be premixed with the compound of the invention prior to application, e.g. as a readymix or tankmix, or by simultaneous application or sequential application to the plant. Suitable rates of attractants are for example 0.02 kg/ha-3 kg/ha.

The compounds of the invention are preferably used for pest control on Faboideae, in particular soybean or lima beans, at 1-500 g/ha, preferably 10-100 g/ha.

The compounds of the invention are suitable for use on any Faboideae plant, such as soybean plants or lima bean plants, including those that have been genetically modified to be resistant to active ingredients such as herbicides or to produce biologically active compounds that control infestation by plant pests.

In a further preferred embodiment, transgenic plants and plant cultivars obtained by genetic engineering methods, if appropriate in combination with conventional methods (Genetically Modified Organisms), and parts thereof, are treated. Particularly preferably, plants of the plant cultivars which are in each case commercially available or in use are treated according to the invention. Plant cultivars are understood as meaning plants having novel properties ("traits") which have been obtained by conventional breeding, by mutagenesis or by recombinant DNA techniques.

These can be cultivars, bio- or genotypes. Depending on the plant species or plant cultivars, their location and growth conditions (soils, climate, vegetation period, diet), the treatment according to the invention may also result in super-additive "synergistic") effects.

Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars (obtained by genetic engineering) which are to be treated according to the invention include all plants which, by virtue of the genetic modification, received genetic material which imparts particularly advantageous, useful traits to these plants.

Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products.

Further and particularly emphasized examples of such traits are a better defense of the plants against animal and microbial pests, such as against insects, mites, phytopathogenic fungi, bacteria and/or viruses, and also increased tolerance of the plants to certain herbicidally active compounds.

Traits that are emphasized in particular are the increased defense of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to herein as "Bt plants"). Traits that are also particularly emphasized are the increased defense of the plants against fungi, bacteria and viruses by systemic acquired resistance (SAR), systemin, phytoalexins, elicitors and resistance genes and correspondingly expressed proteins and toxins.

Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants.

Examples of "Bt plants" are soybean varieties which are sold under the trade names YIELD GARD(®).

Examples of herbicide-tolerant plants which may be mentioned are soya bean varieties which are sold under the trade names Roundup Ready(®) (tolerance to glyphosate), Liberty Link(®) (tolerance to phosphinotricin), IMI(®) (tolerance to imidazolinones) and STS(®) (tolerance to sulphonylureas).

Herbicide-resistant plants (plants bred in a conventional manner for herbicide tolerance) which may be mentioned include the varieties sold under the name Clearfield(®) (for example maize).

Of particular interest are Faboideae, in particular soybean plants, carrying two or more traits (e.g. Enlist®), glyphosate (e.g. Roundup Ready®, Roundup Ready 2 Yield®), sulfonylurea (e.g. STS®), glufosinate (e.g. Liberty Link®, Ignite®), Dicamba (Monsanto) HPPD tolerance (e.g. isoxaflutole herbicide) (Bayer CropScience, Syngenta). Double or triple stack in soybean plants of any of the traits described here are also of interest, including glyphosate and sulfonylurea tolerance (e.g. Optimum GAT®, plants stacked with STS® and Roundup Ready® or Roundup Ready 2 Yield®), dicamba and glyphosate tolerance (Monsanto). Soybean Cyst Nematode resistance soybean (SCN®-Syngenta) and soybean with Aphid resistant trait (AMT®-Syngneta) are also of interest.

These statements also apply to plant cultivars having these genetic traits or genetic traits still to be developed, which plant cultivars will be developed and/or marketed in the future.

Mixtures

The compounds of the invention may be applied in the methods of the present invention in mixtures with fertilizers (for example nitrogen-, potassium- or phosphorus-containing fertilizers). Suitable formulation types include granules of fertilizer. The mixtures preferably contain up to 25% by weight of the compound of the invention.

The compositions of this invention may contain other compounds having biological activity, for example micronutrients or compounds having fungicidal activity or which possess plant growth regulating, herbicidal, insecticidal, nematicidal or acaricidal activity.

The compounds applied in the methods of the present invention may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergize the activity or complement the activity (for example by increasing the speed of effect or overcoming repellency) of the compound of the invention; or help to overcome or prevent the development of resistance to individual components. The particular additional active ingredient will depend upon the intended utility of the composition.

According to one embodiment of the present invention, individual components of the composition according to the invention such as parts of a kit or parts of a binary or ternary mixture may be mixed by the user himself in a spray tank and further auxiliaries may be added, if appropriate.

The compounds of the invention may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Formulations

The invention also relates to agrochemical compositions comprising one or more auxiliary agents and at least one compound of the invention and/or one of its individual embodiments, which are applied in the methods of the present invention.

An agrochemical composition comprises a pesticidally effective amount of a compound of the invention and/or one of its individual embodiments. The term "effective amount" denotes an amount of the composition or of the compounds of the invention, which is sufficient for controlling animal pests on cultivated plants or in the protection of materials and which does not result in a substantial damage to the treated plants. Such an amount can vary in a broad range and is dependent on various factors, such as the pest species to be controlled, the treated cultivated plant or material, the climatic conditions and the specific compound used.

The compounds of the invention can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylaryl sulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound of formula (I) on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Agrochemical compositions containing one or more components of the ginkgo tree according to the invention generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying compound of formula (I) and compositions thereof, respectively, on to plant propagation material, especially seeds include dressing, coating, pelleting, dusting, soaking and in-furrow application methods of the propagation material. Preferably, compound of formula (I) or the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha. In another embodiment the amount is from 0.001 to 0.500 kg/ha, in particular 0.01 to 0.1 kg/ha.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e. g. components comprising compounds of the invention (or one of its individual embodiments) and/or future active substances may be mixed by the user in a spray tank and further auxiliaries and additives may be added, if appropriate.

In a further embodiment, either individual components of the composition according to the invention or partially premixed components can be applied jointly (e.g. after tank mix) or consecutively.

EXAMPLES

The present invention is now illustrated in further details by the following examples, without imposing any limitation thereto.

A. Compounds

Bilobalide, ginkgolide A, ginkgolide B, ginkgolide C and ginkgolide J are commercially available (e.g. from Interchim) and were purchased from commercial sources.

B. Biology

The biological activity and effectivity of the compounds applied in the methods of the invention can be evaluated e.g. in the following assays.

B.1 Green Soldier Stink Bug (*Nezara viridula*)

The active compound is dissolved at the desired concentration in a mixture of 1:1 (vol:vol) distilled water:acetone. Surfactant (Kinetic HV) is added at a rate of 0.01% (vol/vol).The test solution is prepared at the day of use.

Soybean pods were placed in microwavable plastic cups lined with moist filter paper and inoculated with ten 3rd instar N. viridula. Using a hand atomizer, approximately 2 ml solution is sprayed into each cup. Treated cups were kept at about 28-29° C. and relative humidity of about 50-60%. Percent mortality was recorded after 5 days.

In this test, bilobalide, ginkgolide A and ginkgolide B at 500 ppm showed at least 75% mortality in comparison with untreated controls.

In this test, bilobalide, and ginkgolide A at 300 ppm showed at least 75% mortality in comparison with untreated controls.

In this test, bilobalide, and ginkgolide A at 100 ppm showed at least 75% mortality in comparison with untreated controls.

In this test, bilobalide, and ginkgolide A at 10 ppm showed at least 75% mortality in comparison with untreated controls.

B.2 Orchid Thrips (*Dichromothrips corbetti*)

Dichromothrips corbetti adults used for bioassay were obtained from a colony maintained continuously under laboratory conditions. For testing purposes, the test compound is diluted in a 1:1 mixture of acetone:water (vol:vol), plus Kinetic HV at a rate of 0.01% v/v.

Thrips potency of each compound was evaluated by using a floral-immersion technique. All petals of individual, intact orchid flowers were dipped into treatment solution and allowed to dry in Petri dishes. Treated petals were placed into individual re-sealable plastic along with about 20 adult thrips. All test arenas were held under continuous light and a temperature of about 28° C. for duration of the assay. After 3 days, the numbers of live thrips were counted on each petal. The percent mortality was recorded 72 hours after treatment.

In this test, bilobalide, ginkgolide A, ginkgolide B, ginkgolide C and ginkgolide J at 500 ppm showed at least 75% mortality in comparison with untreated controls.

B.3 Brown Stink Bug (*Euschistus heros*)

The active compound is dissolved at the desired concentration in a mixture of 1:1 (vol:vol) distilled water:acetone.

Fresh bean pods were placed in a transparent plastic cup and inoculated with ten adult stage individuals. Insects, food and inside of container are sprayed with 1 ml solution using an air brush. Treated cups were kept at about 25° C. Percent mortality was recorded after 5 days.

In this test, bilobalide at 100 ppm showed at least 75% mortality in comparison with untreated controls.

B.4 Forest shield bug (*Eysarcoris aeneus*)

The active compound is dissolved at the desired concentration in a mixture of 1:1 (vol:vol) distilled water:acetone.

Row peanuts and soybean seeds were placed in a plastic cup and inoculated with ten adult stage individuals. Insects, food and inside of container are sprayed with 1 ml solution using an air brush. After drying, a water supply source will be placed in the cup and the cup closed with a screened lid. Treated cups were kept at about 20° C. Percent mortality was recorded after 5 days.

In this test, bilobalide at 100 ppm showed at least 75% mortality in comparison with untreated controls.

B.5 Rice Leaf Bug (*Trigonotylus caelestialium*)

The active compound is dissolved at the desired concentration in a mixture of 1:1 (vol:vol) distilled water: acetone.

Small wheat seedlings in glass tubes were sprayed with 200 microliter/tube by air brush. After drying, ten 2nd and 3rd nymph stage individuals were released in the tube and the tube closed with a screened lid. Treated cups were kept at about 20° C. Percent mortality was recorded after 5 days.

In this test, bilobalide, and ginkgolide A at 100 ppm showed at least 75% mortality in comparison with untreated controls.

B.6 Brown Stink Bug (*Euschistus heros*)

The active compound is dissolved at the desired concentration in a mixture of 1:1 (vol:vol) distilled water: acetone.

Soybean seedlings of Intacta and BMX-Potencia with one pair of true leaves were sprayed with 2 ml solution using an airbrush. After dry, the plants in small pots were placed inside a transparent plastic cage and infested with 10 adults adult stage individuals. Treated cups were kept at about 25° C. Percent mortality was recorded after 1, 2, and 6 days after application.

In this test, bilobalide at 10 ppm and ginkgolide A at 100 ppm showed the following mortality:

| | | INTACTA | | | | | |
|---|---|---|---|---|---|---|---|
| | dose | mortality (%) | | | mortality (Abbott %)* | | |
| Product | ppm a.i | 1 D.A.A | 2 DAA | 6 DAA | 1 D.A.A | 2 DAA | 6 DAA |
| Untreated | — | 5.0 | 5.0 | 20.0 | — | — | — |
| Ginkgolide A | 100 | 12.5 | 20.0 | 62.5 | 7.9 | 15.8 | 53.1 |
| Bilobalide | 10 | 7.5 | 20.0 | 72.5 | 2.6 | 15.8 | 65.6 |

| | | BMX — POTENCIA | | | | | |
|---|---|---|---|---|---|---|---|
| | dose ppm | mortality (%) | | | mortalty (Abbott %)* | | |
| Product | a.i | 1 D.A.A | 2 DAA | 6 DAA | 1 D.A.A | 2 DAA | 6 DAA |
| Untreated | — | 2.5 | 5.0 | 20.0 | — | — | — |
| Ginkgolide A | 100 | 10.0 | 10.0 | 57.5 | 7.7 | 5.3 | 46.9 |
| Bilobalide | 10 | 5.0 | 7.5 | 60.0 | 2.6 | 2.6 | 50.0 |

DAA = Days After Application
*Corrected mortality according to Abbott, W.S., A method of computing the effectiveness of an insecticide, J. Econ. Entomnal., 18 (1925) 265-267. The test shows that bilobalide and ginkgolide A have a higher efficacy when applied to soybean plants containing a toxin trait of Bacillus thuringiensis (INTACTA) than when applied to genetically modified soybean plants without the Bacillus thuringiensis trait (BMX- POTENCIA). This is surprising since the values in the untreated groups (corrected according to Abbott) are equal, i.e. the Bacillus thuringiensis toxin alone does not control brown stink bugs.

B.7 Green Soldier Stink Bug (*Nezara viridula*)

Lima Bean (*Phaseolus lunatus*, 'Henderson Bush,' Lot #—VR06650) plants were transplanted at the two true-leaf stage into 25.8 cm$^2$ pots filled with sifted (No. 10 sieve) North Carolina loamy sand soil. Pots were held in the greenhouse and watered daily until treatment. Three days after transplant, the compounds were dissolved in acetone and then diluted with water for a final concentration of 50% acetone. Treatments were applied as a drench in 1 ml solution per plant. Plants were held in an environmental chamber (25±2° C., 24 L) and watered as needed for the duration of the test.

Three days after treatment, plants were infested with five 2$^{nd}$ instar nymphs. Plants were covered with organza fabric bags to prevent escape. Four days after infestation, the number of live nymphs on each plant was recorded, and means were calculated for each treatment. The percent control was calculated as the percent mortality relative to the solvent blank.

In this test, bilobalide, and ginkgolide A at 300 g ai/ha showed at least 75% mortality in comparison with untreated controls.

B.8 Green Soldier Stink Bug (*Nezara viridula*)

Pots (25.8 cm$^2$) were filled with a 1:1 mixture of sifted (No. 10 sieve) North Carolina loamy sand soil and play sand. Technical material was dissolved in DMSO in a 20 ml scintillation vial. A total application volume of 25 µl of solution was added to a 20 ml vial, ten lima bean seeds (*P. lunatus*) were added, and the vial was vortexed for 1 minute. Seeds were allowed to dry and planted at a depth of 2 cm later the same day. One seed was planted per pot. Pots were held in the greenhouse and watered daily until infestation.

Ten days after treatment, plants were infested with five 2$^{nd}$ instar nymphs. Plants were covered with organza fabric bags to prevent escape. Plants were held in an environmental chamber (25±2° C., 24 L) and watered as needed.

Four days after infestation, the number of live nymphs on each plant was recorded, and means were calculated for each treatment. The percent control was calculated as the percent mortality relative to the solvent blank.

In this test, ginkgolide A at 0.063 mg ai/seed showed at least 75% mortality in comparison with untreated controls.

We claim:

1. A method for controlling pests of genetically modified soybean plants, comprising contacting the soybean plant, parts of it, its propagation material, the pests, their food supply, habitat or breeding grounds with one or more components of the ginkgo tree selected from the group consisting of bilobalide, ginkgolide A, ginkgolide B, ginkgolide C, ginkgolide J and ginkgolide M wherein the soybean plants have at least one toxin of *Bacillus thuringiensis* formed in the plant; and wherein the pests are from the family of Pentatomidae and/or Thripidae.

2. The method of claim 1, wherein the pests are *Acrosternum* spp., *Euschistus* spp., *Nezara* spp. and/or *Piezodrus* spp.

3. The method of claim 1, wherein the pests are *Acrosternum hilare, Euschistus heros, Nezara viridula* and/or *Piezodrus guildini*.

4. The method of claim 1, wherein the component or components of the ginkgo tree are applied in an amount of from 1 to 500 g/ha.

5. The method of claim 1, wherein the components of the ginkgo tree are applied by foliar application.

6. The method of claim 1 for protecting plant propagation material.

7. The method of claim 1, wherein the components of the ginkgo tree are applied to soybean plants that have at least one gene selected from CrylA(a), CrylA(b), CrylA(c), CryllA, CrylllA, CryIIIB2, Cry9c, Cry2Ab, Cry3Bb and CrylF, or a combination thereof.

8. The method of claim 1, wherein the pests are resistant to one or more of the insecticides selected from the group consisting of pyrethroids, neonicotinoids, and organophosphates.

9. The method of claim 1, wherein the pests are selected from *dichromothrips* sp.

10. The method of claim 1, wherein the soybean plant has an increased tolerance to certain herbicidally active compounds.

* * * * *